United States Patent [19]

Bennett

[11] Plant 4,922

[45] Nov. 9, 1982

[54] MINIATURE ROSE PLANT

[76] Inventor: Cecilia L. D. Bennett, 489 Minot Ave., Chula Vista, Calif. 92010

[21] Appl. No.: 213,739

[22] Filed: Dec. 5, 1980

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the bright orange bloom with a distinct yellow eye when in open bloom.

1 Drawing Figure

1

The present invention relates to a new and distinct variety of a bush type rose plant of miniature class; the variety showing a strong resemblance to its seed parent, Contempo, (U.S. Plant Pat. No. 3,102) an orange blend florabunda.

The variety is further characterized by:

An abundance of bloom, with flowers usually borne one to a stem.

No discernable fragrance.

The plant is very vigorous, with a tendancy to be rangy but well branched; small foliage with pointed semi glossy leaflets; the buds and flowers being similar in form to Pink Petticoat (introduced in 1979).

The plant, which has an average height of 18"-24" or more, can be contained to a smaller size with occasional trimming.

A plant which grows and blooms satisfactorily both in the greenhouse and outdoors; is good for growing in pots; and provides excellent color as a garden decoration as well as a cut flower.

The present variety of miniature rose was originated by me at Tiny Petal's Nursery located at Chula Vista, Calif., under conditions of careful control and observation, as a cross between Contempo (U.S. Plant Pat. No. 3,102) as the seed parent Sheri Anne (miniature — U.S. Plant Pat. No. 3,826) as the pollen parent.

Subsequent to origination of the variety I successfully reproduced it, at Tiny Petal's Nursery located at aforesaid, by budding as well as by cuttings; the reproductions running true in all respects.

The color photograph illustrates the variety, including the foliage, buds and flowers.

Referring now specifically to the new and distinct variety of miniature rose plant, the following is a detailed description thereof in outline: all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Lelia Laird.

Flowers borne: Usually one to a stem.

Quantity of bloom: Abundant both outside and in greenhouse.

Bud:

2

Peduncle.—Medium to long; sturdy; erect; medium green and reddish-green depending on conditions.

*Hairs.*—Numerous; minute; reddish.

*Before calyx breaks.*—Size — small. Form short; pointed with several foliaceous appendages and numerous tiny hairs on surface of bud; with foliaceous parts extending beyond the tip of the bud equal to one-half or less of its length. Color — medium green with reddish tinge.

*As calyx breaks.*—Color orange with yellow at the base. Opens well in all weather.

Bloom:

*Size when fully open.*—Small, 1½ to 2 inches.

*Petalage.*—Double — 25 to 35 petals, arranged regularly plus sometimes several small petaloids.

*Form.*—High centered; exhibition; bloom opens to reveal stamens surrounded by a large yellow eye in the center.

Petals: Fairly thick; matte finish on inside and outside surface.

*Shape.*—Outside petals, broad lanceolate with acute tip; intermediate — broad lanceolate with acute tip; inside petals — round with acute tip; a few petaloids in the center.

Color: Newly opened flower from a plant grown outdoors at Chula Vista, Calif.:

*Outer petals, upper surface.*—Outer half, near carmine 21/2 page 21. Lower half, near saffron yellow 7/2 page 7.

*Outer petals, under surface.*—Outer half near scarlet 19/2 page 19, lower half near saffron yellow 7/2 page 7.

*Intermediate petals, upper half.*—Outer half near carmine 21/2 page 21. Lower half, near chrome yellow 605 page 144.

*Intermediate petals, under surface.*—Outer half, near geranium red 20/1 page 20. Lower half, near saffron yellow 7/2 page 7.

*Inner petals, under surface.*—Outer half, near carmine 21/1 page 21. Lower half, near chrome yellow 605 page 144.

*Inner petals, under surface.*—Outer half, near geranium red 20/1 page 20. Lower half near saffron yellow 7/2 page 7.

Behaviour: Opens well in all weather. Color retains its brilliance and beauty about a week at which time the petals fall. Flower longevity seven to ten days, when grown in pot. Cut flowers at room temperature four to five days.

Reproductive organs:

*Stamens.*—Abundant, arranged regularly around pistil.

*Filaments.*—Varying lengths, average length, yellow.

*Anthers.*—Well formed; yellow.

*Pollen.*—Abundant.

*Pistils.*—Average amount, red filaments.

*Styles.*—Fairly even; medium to short; bunched; color — greenish.

*Ovaries.*—All encased in calyx.

*Hips.*—Some.

*Sepals.*—Permanent; spear shaped; recurve against peduncle.

*Seed.*—A few.

Foliage:

*Leaves.*—Compound of five; leaflets fairly small;

*Leaflets.*—Shape: broad, apex acute; arrow shaped.

*Margin.*—Serrated.

*Color.*—Medium green; reddish-brown in the fall.

*Rachis.*—Medium; grooved; underside, small amount of hairs. A few prickles.

Stipules: Medium long; narrow to medium width; narrow points which turn upwards.

Growth:

*Habit.*—Dwarf; bushy, rangy; much branched.

*Growth.*—Free vigorous.

*Canes.*—Long; slender; sturdy.

*Main stems.*—Color: medium green.

*Thorns.*—A few; slender, straight, reddish-brown.

*Prickles.*—None.

i Hairs.—None.

Branches:

*Color.*—Medium green.

*Thorns.*—A few; medium length; slender.

*Prickles.*—None.

*Hairs.*—None.

The miniature rose plant and its flowers herein described may vary in slight detail due to climatic, soil and cultural conditions under which the variety may be grown; the present description being of the variety as grown at Chula Vista, Calif.

The following is claimed:

1. A new and distinct variety of miniature rose plant of hardy, dwarf, bushy, upright, much branched habit, substantially as illustrated and described, characterized by buds and flowers of a carmine color, and further characterized by a plant of vigorous and upright growth habit, easy to propagate from cuttings or by budding, with an abundance of small to medium glossy foliage and an abundance of flowers borne singularly on upright sturdy stems.

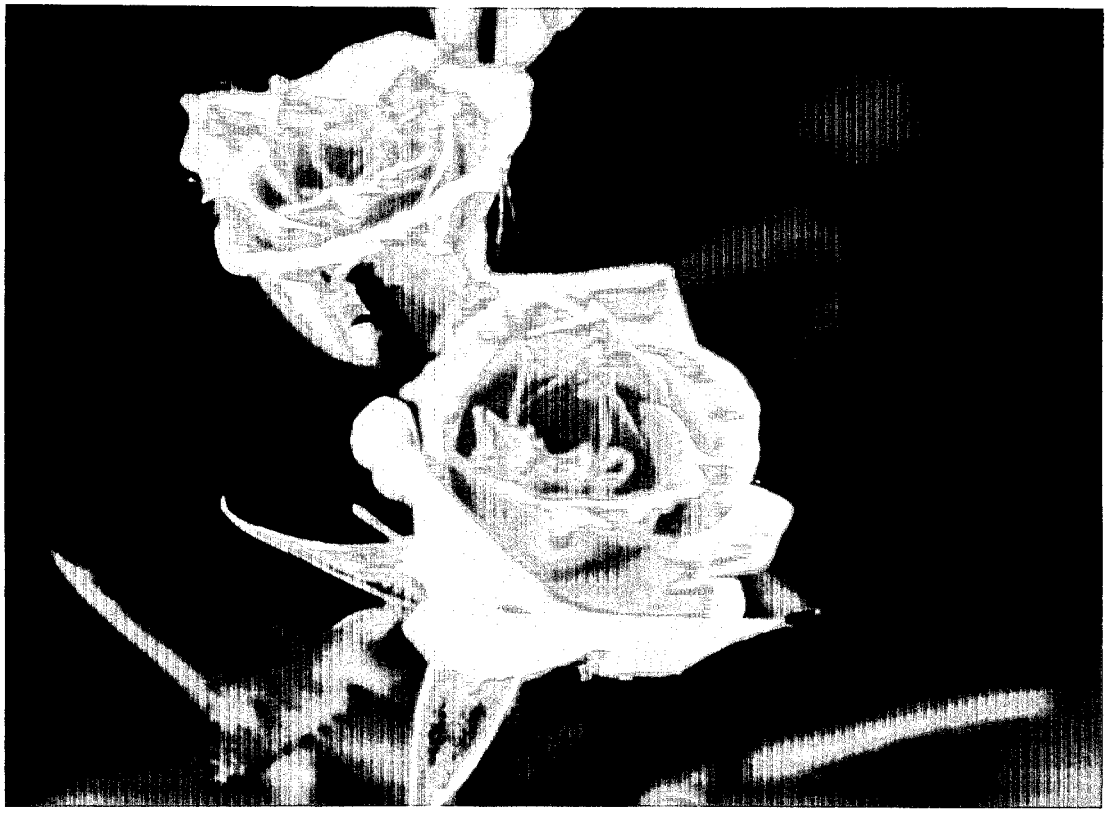

* * * * *